(12) United States Patent
Boutoussov et al.

(10) Patent No.: US 11,173,010 B2
(45) Date of Patent: Nov. 16, 2021

(54) LASER CONTROL GUI SYSTEM AND METHOD

(71) Applicant: BIOLASE, INC., Irvine, CA (US)

(72) Inventors: Dmitri Boutoussov, Dana Point, CA (US); Douglas Patton, Costa Mesa, CA (US)

(73) Assignee: BIOLASE, INC., Irvine, CA (US)

( * ) Notice: Subject to any disclaimer, the term of this patent is extended or adjusted under 35 U.S.C. 154(b) by 447 days.

(21) Appl. No.: 15/719,137

(22) Filed: Sep. 28, 2017

(65) Prior Publication Data

US 2018/0085188 A1 Mar. 29, 2018

Related U.S. Application Data

(60) Provisional application No. 62/400,954, filed on Sep. 28, 2016.

(51) Int. Cl.
*A61C 1/00* (2006.01)
*G06F 3/0484* (2013.01)
(Continued)

(52) U.S. Cl.
CPC ............ *A61C 1/0046* (2013.01); *A61B 18/22* (2013.01); *A61C 1/0015* (2013.01);
(Continued)

(58) Field of Classification Search
CPC ... A61C 1/0046; A61C 1/0015; A61C 1/0061; A61B 18/22; G06F 3/04847
(Continued)

(56) References Cited

U.S. PATENT DOCUMENTS 5,290,274 A * 3/1994 Levy .................. A61B 18/20
606/13
5,833,683 A * 11/1998 Fuller .................. A61B 18/22
606/17
(Continued)

FOREIGN PATENT DOCUMENTS

KR 10-2012-0013369 A 2/2012
WO 2008061225 A2 5/2008

OTHER PUBLICATIONS

Fantarella et al., The 9.39.3-µm $CO_2$ Dental Laser: Technical Development and Early Clinical Experiences, Scientific Review 2014, pp. 1-18. (Year: 2014).*

(Continued)

*Primary Examiner* — William D Titcomb
(74) *Attorney, Agent, or Firm* — Greenberg Traurig, LLP

(57) ABSTRACT

Some embodiments include a dental laser system with a controller coupled to an electromagnetic energy source, where the controller's graphical user interface enables a user to provide input to control operating parameters of the electromagnetic energy source. In some embodiments, the graphical user interface can render a controller enabling user control of a plurality dental laser system parameters with a single action or input. In some embodiments, the user's interaction with a graphical portion of the controller sufficient to control more than one operational parameter of the dental laser system without a requirement for the user to provide an additional or substantially simultaneous interaction with any other controller or portion of the graphical user interface. Further, the graphical content has a graphic indicative of a mode, an operational status, and/or an operational parameter of the dental laser system that is displayed, updated, or animated by the controller.

19 Claims, 6 Drawing Sheets

(51) Int. Cl.
*A61B 18/22* (2006.01)
*G06F 3/0481* (2013.01)
*G06F 3/0482* (2013.01)
*G06F 3/0488* (2013.01)
*A61C 1/05* (2006.01)
*A61B 18/20* (2006.01)

(52) U.S. Cl.
CPC ........ *A61C 1/0061* (2013.01); *G06F 3/04847* (2013.01); *A61B 2018/2065* (2013.01); *A61C 1/052* (2013.01); *G06F 3/0482* (2013.01); *G06F 3/0488* (2013.01); *G06F 3/04817* (2013.01); *G06F 3/04845* (2013.01)

(58) Field of Classification Search
USPC ........................................................ 715/700
See application file for complete search history.

(56) References Cited

U.S. PATENT DOCUMENTS

| | | | |
|---|---|---|---|
| 6,663,386 B1 * | 12/2003 | Moelsgaard | A61C 1/0046 |
| | | | 433/215 |
| 6,677,965 B1 * | 1/2004 | Ullmann | G06F 3/04812 |
| | | | 715/786 |
| 7,485,116 B2 | 2/2009 | Cao | |
| 8,204,612 B2 | 6/2012 | Feine et al. | |
| 8,337,097 B2 | 12/2012 | Cao | |
| 8,670,858 B2 | 3/2014 | Feine et al. | |
| 8,834,457 B2 | 9/2014 | Cao | |
| 8,961,040 B2 | 2/2015 | Cao | |
| 8,967,883 B2 | 3/2015 | Cao | |
| 9,052,805 B2 | 6/2015 | Boutoussov et al. | |
| 9,551,995 B2 | 1/2017 | Feine et al. | |
| 9,696,893 B2 | 7/2017 | Boutoussov et al. | |
| 9,864,485 B2 * | 1/2018 | Patton | G06F 3/04842 |
| 2006/0064080 A1 | 3/2006 | Cao | |
| 2008/0032251 A1 * | 2/2008 | Chou | A61C 1/0046 |
| | | | 433/29 |
| 2008/0086117 A1 | 4/2008 | Cao | |
| 2008/0154249 A1 | 6/2008 | Cao | |
| 2008/0161783 A1 | 7/2008 | Cao | |
| 2010/0036535 A1 | 2/2010 | Feine et al. | |
| 2010/0167226 A1 * | 7/2010 | Altshuler | A61B 18/20 |
| | | | 433/29 |
| 2010/0281636 A1 | 11/2010 | Ortins et al. | |
| 2012/0171657 A1 | 7/2012 | Ortins et al. | |
| 2013/0036384 A1 * | 2/2013 | Murata | G06F 3/0482 |
| | | | 715/815 |
| 2013/0045456 A1 | 2/2013 | Feine et al. | |
| 2013/0103121 A1 | 4/2013 | Cao | |
| 2013/0103122 A1 | 4/2013 | Cao | |
| 2013/0104071 A1 * | 4/2013 | Boutoussov | G06F 3/0481 |
| | | | 715/781 |
| 2013/0231649 A1 | 9/2013 | Cao | |
| 2013/0323672 A1 * | 12/2013 | Monty | A61C 1/0069 |
| | | | 433/29 |
| 2014/0170588 A1 | 6/2014 | Miller et al. | |
| 2014/0363784 A1 * | 12/2014 | Monty | A61C 1/0046 |
| | | | 433/29 |
| 2015/0057063 A1 * | 2/2015 | Tollstedt | G07F 17/3209 |
| | | | 463/13 |
| 2015/0167144 A1 * | 6/2015 | Shijie | B23K 35/404 |
| | | | 427/560 |
| 2015/0183042 A1 * | 7/2015 | Scotchmer | C23C 4/10 |
| | | | 427/580 |
| 2015/0277738 A1 | 10/2015 | Boutoussov et al. | |
| 2016/0278860 A1 | 9/2016 | Cao | |
| 2016/0299510 A1 | 10/2016 | Feine et al. | |
| 2017/0215989 A1 * | 8/2017 | Gregg, II | A61C 8/0006 |
| 2017/0274220 A1 * | 9/2017 | Ertl | A61N 5/0603 |
| 2017/0300220 A1 | 10/2017 | Boutoussov et al. | |
| 2018/0104020 A1 * | 4/2018 | Boutoussov | A61C 1/0015 |

OTHER PUBLICATIONS

Korean Intellectual Property Office; PCT International Search Report, Issued in Connection to PCT/US2017/054101; dated Jan. 11, 2018; 4 pages; Korea.

Korean Intellectual Property Office; PCT Written Opinion of the International Searching Authority, Issued in Connection to PCT/US2017/054101; dated Jan. 11, 2018; 4 pages; Korea.

English Translation of Abstract for KR10-2012-0013369; Feb. 14, 2014; 2 pages; Korea.

* cited by examiner

LASER CONTROL GUI SYSTEM AND METHOD

RELATED APPLICATIONS

This application claims priority to United States provisional application Ser. No. 62/400,954, filed on Sep. 28, 2016, the entire contents of which are incorporated herein by reference.

BACKGROUND

The increasing range and sophistication of dental laser tools has broadened their appeal within the dental community. Many dental practices currently have at least one complex dental laser station that typically includes control systems, displays, and one or more user interfaces of various forms that are used to control the tool, and/or monitor and communicate some function or operational characteristic of the tool. The dental laser station may include different electromagnetic energy sources that output different wavelengths of light that can be used together in performing various procedures. The dentist may be presented with options for adjusting one or more operating parameters of one or more of the electromagnetic energy sources depending on the procedure.

However, in most systems available on the market today, the user interface is often complex, and typically does not enable the dentist to choose or update multiple operational characteristics of the laser station and/or to recall one or more specific parameters tailored for a specific clinical application. This can be especially troublesome when a user wishes to enter a setup for a specific clinical protocol. A user can adjust parameters for a particular clinical application following guidelines from manufacturer, a particular educational program, or by following their own ideas based on experience and education. In some instances, presets may enable the user to select particular clinical applications using pre-programmed sets of parameters. However, some complex procedures may contain several step-by-step pre-programmed settings with certain names and performance guidelines, where only some systems enable the user to deviate from factory pre-set parameters.

SUMMARY

Some embodiments include a dental laser system comprising at least one electromagnetic energy source, and at least one controller coupled to the at least one electromagnetic energy source. In some embodiments, the controller includes a graphical user interface configured to enable a user to provide input to the controller to control at least one operating parameter of the at least one electromagnetic energy source, where under control of the controller, the graphical user interface is configured and arranged to render graphical content. In some embodiments, the graphical content comprises a master controller configured and arranged to enable a user to control a plurality of parameters of the dental laser system with a single action or input to the graphical user interface. In some embodiments, this involves the user's interaction with a graphical portion of the master controller sufficient to control more than one operational parameter of the dental laser system without a requirement for the user to provide an additional or substantially simultaneous interaction with any other adjacent controller or graphical portion of the graphical user interface. Further, in some embodiments, the graphical content comprises at least one graphic indicative of a mode, an operational status, and/or an operational parameter of the dental laser system, where the at least one graphic is displayed, updated, or animated by the at least one controller.

In some embodiments, the at least one graphic includes at least one icon, textural display, or graphical update that is displayed, updated, or animated by the at least one controller based at least in part on the user's interaction with the graphical portion of the master controller. In some embodiments of the invention, the master controller comprises a slider. In some embodiments, the slider comprises a laser energy control slider, a laser pulse width slider, at least one fluid delivery control slider, an aiming slider, and an illumination slider.

In some embodiments, the master controller comprises a single slider as the only slider displayed on the graphical user interface. In some further embodiments, the master controller comprises a single slider displayed to the user with at least one other slider displayed elsewhere in the graphical user interface. In some embodiments, the master controller is configured to move the at least one other slider based at least in part on the user's interaction with the graphical portion of the master controller.

In some embodiments, the controller is configured to move at least a graphical portion of the at least one other slider at the same rate as the controller moves at least a graphical portion of the master controller based at least in part on the user's interaction. In some embodiments, the controller is configured to move at least a graphical portion of the at least one other slider at a different rate than the controller moves at least a graphical portion of the master controller based at least in part on the user's interaction.

Some embodiments include a slider is positioned on a slide bar, where the slider is moveable on the slide bar based on user input. In some embodiments, the user input includes dragging the slider on the slide bar. In some further embodiments, the user input includes actuating a "+ve" or "−ve" end of the slide bar.

In some embodiments, the graphical content includes a substantially circular central display at least partially encircled by a rendered substantially circular outer display. In some embodiments, the outer display comprises a substantially circular control wheel including a plurality of segments selectable by a touch of a user. In some embodiments, the circular control wheel includes a display of treatment categories, treatment procedures or laser control options on at least some of the plurality of segments. In some embodiments, upon selection of a segment, the controller is configured and arranged to render the segment with a distinguishing graphical look based on the touch of the user.

Some embodiments include a favorite selection icon providing an option to favorite a procedure and/or step of a procedure. In some further embodiments, the control wheel comprises at least one user-defined or selected favorite dental procedures or favorite steps of a dental procedure represented as at least one of the user-selectable segments. In some embodiments, the central display includes an operating parameters display of laser energy, laser power, a pulse frequency, air delivery, and water delivery. In some further embodiments, the master controller comprises a single slider as the only slider displayed on the graphical user interface, and where movement of the single slider by a user results in the controller substantially simultaneously updating the operating parameters display of laser energy, laser power, a pulse frequency, air delivery, and water delivery.

DETAILED DESCRIPTION

Figure 1:
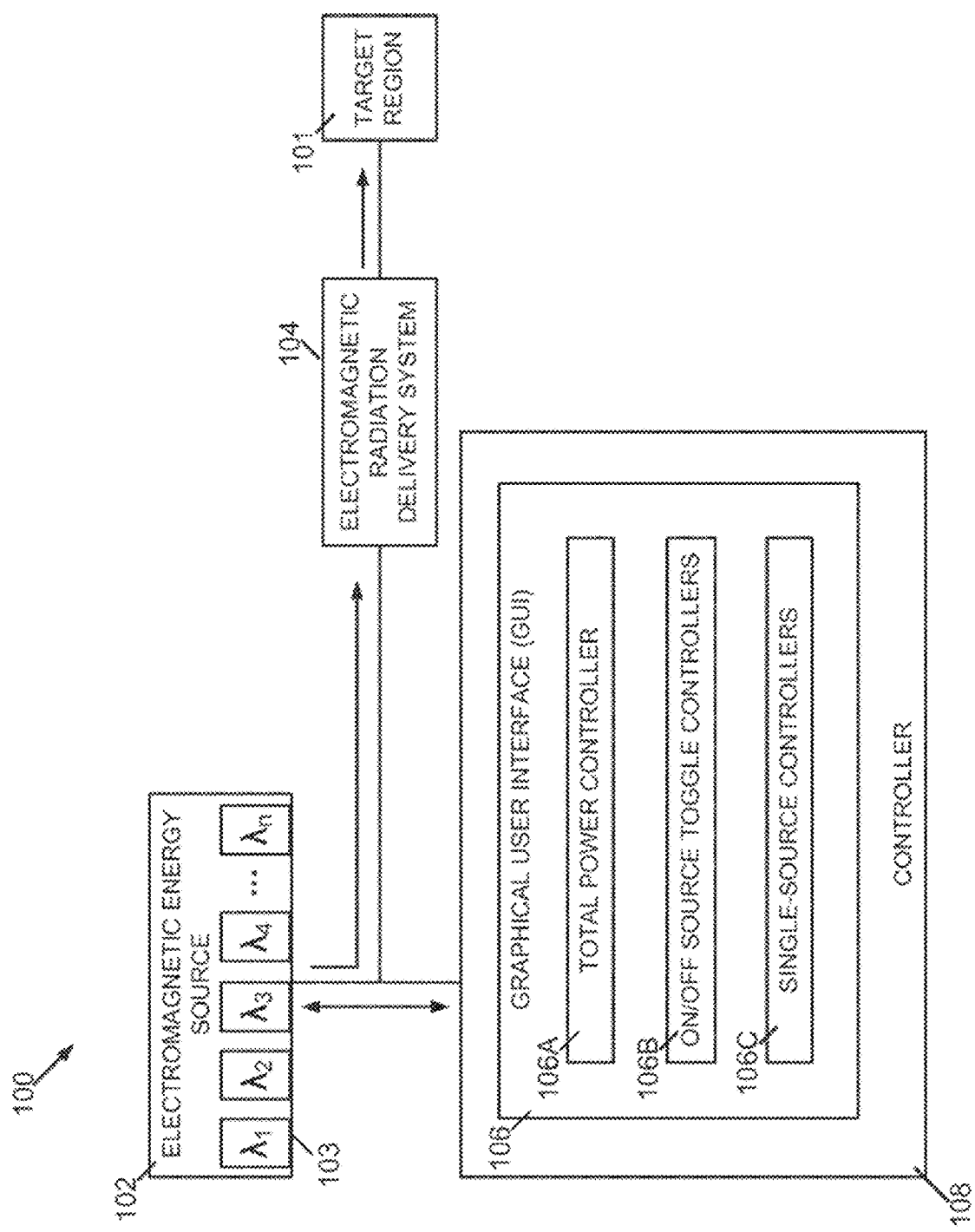
FIG. 1 illustrates a block diagram of an example system including a graphical user interface (GUI) for controlling an electromagnetic energy source having a plurality of laser sources in accordance with some embodiments of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments, and are not intended to limit the scope of embodiments of the invention. Skilled artisans will recognize the examples provided herein have many useful alternatives that fall within the scope of embodiments of the invention.

Some embodiments include a computer-implemented method for controlling a plurality of electromagnetic energy sources. In some embodiments, the computer-implemented method is embodied as a computer-program product. Some embodiments provide a computer-program product for controlling a plurality of electromagnetic energy sources, tangibly embodied in a machine-readable storage medium, includes instructions configured to cause a data processing apparatus to perform operations. In a computer-implemented method for controlling a plurality of electromagnetic energy sources, instructions are executed on a processor to display a user interface region on a computer-human interface display device. Some further embodiments provide a system for controlling a plurality of electromagnetic energy sources including one or more processors. The system can also include one or more computer-readable storage mediums containing instructions configured to cause the one or more processors to perform operations. In some embodiments, the operations include displaying a user interface region on a computer-human interface display device. The user interface region can include a control wheel configured to display a total output power of the plurality of the electromagnetic energy sources. In some embodiments, the user interface region includes a control wheel that can be configured to control a plurality of the adjustable parameters and monitor the functional aspects of a dental laser station. In some embodiments, an input is received via the user interface region, where the input is an interaction with a single control feature to affect one or more adjustable parameters that can include, but not be limited to, laser pulse peak power, laser pulse repetition rate, laser pulse duration, laser average output power, and volume and quality of the cooling water spray or air flow. In some embodiments, the adjustable parameters can be assigned or selected as one or more favorites comprising one or more variables, parameters or guidelines.

Some embodiments of the invention described herein include systems and methods to enable the control and/or monitoring of complex dental laser stations using interfaces that can be customized or easily changed using a single or master control. Some embodiments of the invention include control systems, displays, and associated user interfaces that can be used to control some aspect of a dental laser station, and/or communicate some function or operational characteristic of the tool to the user. For example, some embodiments include control systems, displays, and user interfaces that can be used to control dental laser stations or related dental restoration and/or oral disease prevention tools. More specifically, the various embodiments of the invention described herein include systems and methods to enable an operator to operate and/or monitor the functional aspects of dental laser stations using one or more graphical interfaces or displays. Further, some embodiments include graphical interfaces or displays can be customized for a specific dental procedure and/or for any specific dental specialty including, but not limited to general dentistry, oral and maxillofacial dentistry, orthodontic dentistry, endodontic dentistry, pediatric dentistry, cosmetic dentistry, and so on. One of ordinary skill in the art will recognize that the example embodiments described herein are in no way limited to the field of dentistry, but can be used in other medical fields including surgery such as cosmetic or dermatological surgery and/or treatments.

Some embodiments of the invention include a graphical user interface (hereafter "GUI") and systems and methods that generate the GUI. In some embodiments, the GUI can comprise one or more display windows and/or menus that can be organized based upon a one or more GUI category buttons. In some embodiments, any one or more of the GUI category buttons can have one or more control system attributes or functions. In other words, any one or more of the GUI category buttons can have one or more control system attributes or functions that can be accessed by a user (e.g., by touching the display screen on or adjacent to the GUI category buttons). In some embodiments, any one or more of the GUI category buttons can be used to control a plurality of system attributes or functions using a single action or input from a user. In some embodiments, the GUI can comprise a 4K, 4K-Ultra HD, and/or 8K display.

In some embodiments, the category buttons can be used to select or control specific clinical categories enabling an organized workflow. In some embodiments, the category buttons can be defined as, but not limited to, dentin, enamel, anterior deciduous, hemostasis, perio, endo, incision/excision, de-sensitization and/or osseous. Throughout the description and in the illustrations of FIGS. 4-6 described below, GUI displays can comprise "soft" buttons that can be graphically rendered on a display, and/or can be hard buttons adjacent to one or more displays. In some embodiments, both "soft" and "hard" buttons can be used. In some embodiments, the "soft" and/or "hard" buttons can be positioned on a dental tool or associated control equipment and/or a remote control or a WiFi linked system.

Some embodiments of the invention include at least one GUI that is rendered on and/or is contained within a touchscreen display. For example, in some embodiments, the display can comprise a touchscreen display configured to enable a user to interact with the displayed GUI. In some embodiments, user interactions with the GUI can include contact of at least a portion of the display to initiate or represent an input to the display and/or an input or selection of any information within the display or GUI. For example, in some embodiments, a user, using single, multiple, or repeated physical contact with the display, can initiate one or more functions of the dental laser station. In some embodiments, using one or more portions of the GUI, a user can enter, select, and/or modify one or more system or operational variables or attributes. For example, in some embodiments, using at least one displayed feature, a user can use the GUI to control a plurality of system or operational variables, attributes, or functions. In some embodiments, the GUI can be used to control a plurality of system or operational variables, attributes, or functions interactively (e.g., in real time or substantially real time) to adjust and optimize the operational characteristics of a dental laser (e.g., in real time or substantially real time). In some embodiments, the GUI can be used to control a plurality of system or operational variables, attributes, or functions prior to starting a dental procedure, during a dental procedure, and/or after a dental procedure has been performed.

In some embodiments of the invention, the system and/or the GUI can be coupled to and/or can include at least one dental laser. In some embodiments, the dental laser can comprise one or more different lasers, one or more different laser diodes, and/or one or more different sources of light. In some embodiments, the laser sources can include, but are not limited to, an erbium, yttrium, aluminum garnet (Er: YAG) solid state laser; a chromium, thulium, erbium, yttrium, aluminum garnet (CTE:YAG) solid state laser; an erbium, yttrium orthoaluminate (Er:YAL0$_3$) solid state laser; a holmium, yttrium, aluminum garnet (Ho:YAG) solid state laser; a quadrupled neodymium, yttrium, aluminum garnet (quadrupled Nd:YAG) solid state laser; an excimer laser; or a carbon dioxide ($CO_2$) laser. In some further embodiments of the invention, the dental laser can include one or more erbium, chromium, yttrium, scandium, gallium garnet lasers (including for example a Er:Cr:YSGG laser).

In some embodiments of the invention, the GUI can comprise one or more displayed menus. In some embodiments, one or more of the displayed menus can be navigated by user to control or monitor one or more system or operational variables, attributes, or functions of one or more dental lasers. For example, FIG. 1 illustrates a block diagram of an example system 100 that includes a graphical user interface (GUI) 106 that can be configured and/or used to control at least one electromagnetic energy source 102. In some embodiments, the electromagnetic energy source 102 can include one or a plurality of laser sources 103. The example embodiments of the system 100 of FIG. 1, the electromagnetic energy source 102 includes an "n" number of separate laser sources 103 (e.g., an "n" number of solid-state lasers, and/or laser diodes, and/or other light sources). Further, in some embodiments, the "n" number of separate laser sources 103 can be configured to produce electromagnetic radiation at different wavelengths $\lambda 1$, $\lambda 2$, $\lambda 3$, $\lambda 4$, . . . $\lambda n$. For example, in some embodiments, where n is equal to one, the electromagnetic energy source 102 can include a single laser source 103 with a single wavelength, and where n is greater than one, the electromagnetic energy source 102 can comprise multiple wavelength.

Figure 2:
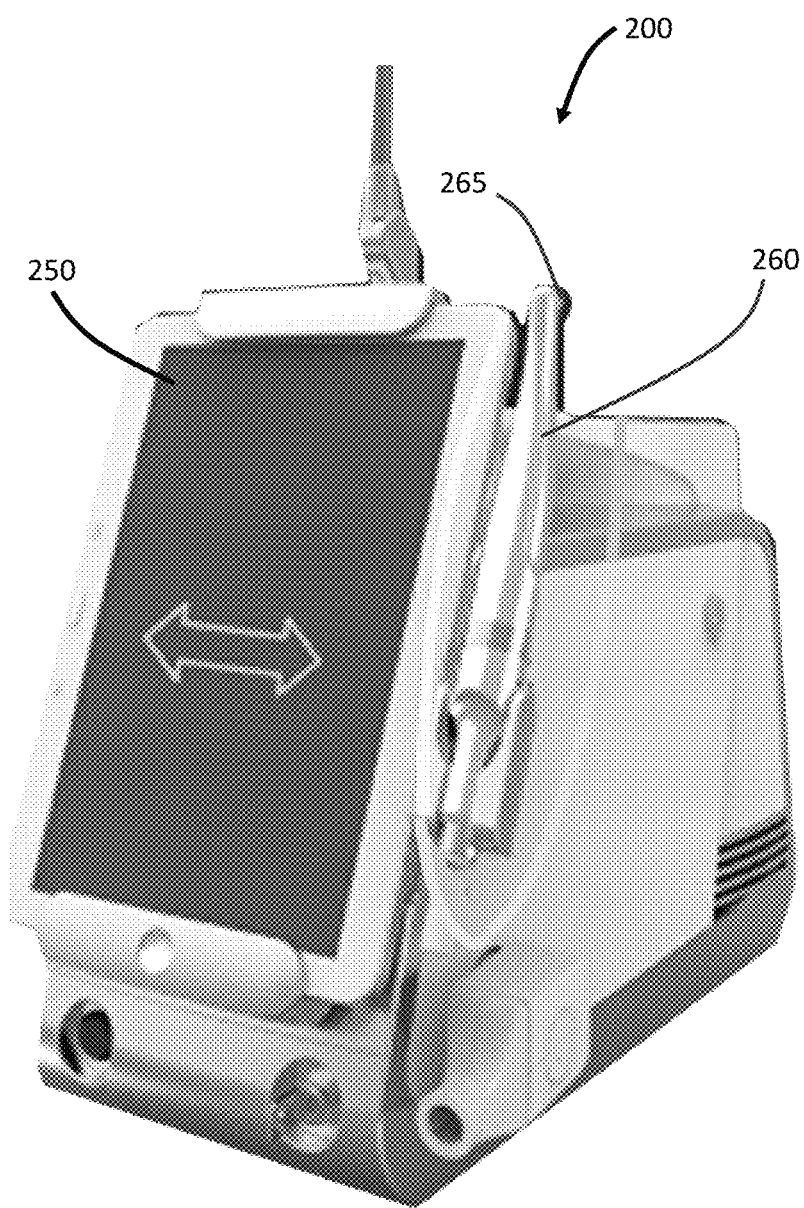
FIG. 2 depicts an example of a dental laser station including a display configured for rendering of a GUI using the system of FIG. 1 in accordance with some embodiments of the invention.

In some embodiments, the different wavelengths of the n laser sources 103 can be utilized to perform a variety of different procedures (e.g., simultaneous teeth-whitening and gum treatment in a dental procedure, where the teeth-whitening and the gum treatment procedures each utilize a different wavelength of light). One non-limiting example or a dental laser system that can incorporate, integrate, or be coupled to the n laser sources 103 is shown in FIG. 2 which depicts an example of a dental laser station 200 including a display 250 configured for rendering of a GUI using the system of FIG. 1 in accordance with some embodiments of the invention. In some embodiments, the display 250 can render a GUI that can include at least one menu that can comprise one or more user-adjustable features that can be used to operate the dental laser station 200. In some embodiments, any one or more of the GUI's including any one or more of the functions and/or attributes of any one or more of the GUI's described herein can be rendered using the display 250 of the dental laser station 200.

In some embodiments of the invention, the electromagnetic energy source 102 can be coupled to both an electromagnetic radiation delivery system 104 and a controller 108. In some embodiments, the GUI 106 of FIG. 1 can be rendered by the display 250 under the control of the controller 108. In some embodiments, the electromagnetic radiation delivery system 104 can route the electromagnetic energy generated by the n sources 103 to a target region 101. For example, in some embodiments, the electromagnetic radiation delivery system 104 can be and/or can include the handpiece 260, and electromagnetic energy can be delivered from the n sources 103 to a target region 101 by a tip 265 of the handpiece 260. In some embodiments, the target region 101 can be an area to which the electromagnetic energy is ultimately delivered and can be, for example, an area of the mouth (e.g., an area including teeth and gums) or another area of a human body or other mammal. In some embodiments, the electromagnetic radiation delivery system 104 can be, for example, one or more multi-mode fiber optic cables configured to guide the output of the n laser sources 103. Further, in some embodiments, the electromagnetic radiation delivery system 104 can also be an instrument (e.g., a medical or dental instrument) configured to output the light of the n different wavelengths. In some embodiments, the handpiece 260 can comprise the one or more multi-mode fiber optic cables configured to guide the output of the n laser sources 103 and/or can be the instrument (e.g., a medical or dental instrument) configured to output the light of the n different wavelengths of the n laser sources 103.

In some embodiments of the invention, the controller 108 can be coupled to the electromagnetic energy source 102, and can be used to control the output of the n laser sources 103. In some embodiments, the controller 108 can include the GUI 106, which can include various controls to enable a user to operate or monitor a function of a dental laser station (e.g., such as dental laser station 200). For example, some embodiments include a total power controller 106A, and/or on/off source toggle controllers 106B, and/or single-source controllers 106C. In some embodiments of the invention, the total power controller 106A can be configured to display and to allow a user to control a total output power of the n laser sources 103. In some embodiments, the total output power can be controlled on the fly.

In some embodiments, the an output power (e.g., total output power) of the n laser sources 103 can be a combined output power determined by summing the output powers of each of the individual n laser sources 103. In some embodiments, an input from the user can be received via the GUI 106, where the input can be a user-interaction with one or more of portions of the GUI 106 that represent the total power controller 106A, and/or the on/off source toggle controllers 106B, and/or the single-source controllers 106C. In some embodiments, based on the input from the user, a power output of one or more of the n laser sources 103 can be adjusted. Thus, by interacting with one or more portions of the GUI 106, the user can be enabled to control the total (i.e., combined) output power of the n laser sources 103, as well as the output power of each of the n sources 103 individually. In some embodiments of the invention, the interaction can utilized a single element or portion of a rendered display of the GUI 106. For example, in some embodiments, an input from the user can be received via the GUI 106, where the input can be a user-interaction with a single rendered element on the GUI 106. In some embodiments, the single element can represent the total power controller 106A, and/or the on/off source toggle controllers 106B, and/or the single-source controllers 106C. In some embodiments, based on the input from the user, a power output of one or more of the n laser sources 103 can be adjusted following only the user's interaction with the single rendered element.

Figure 3:
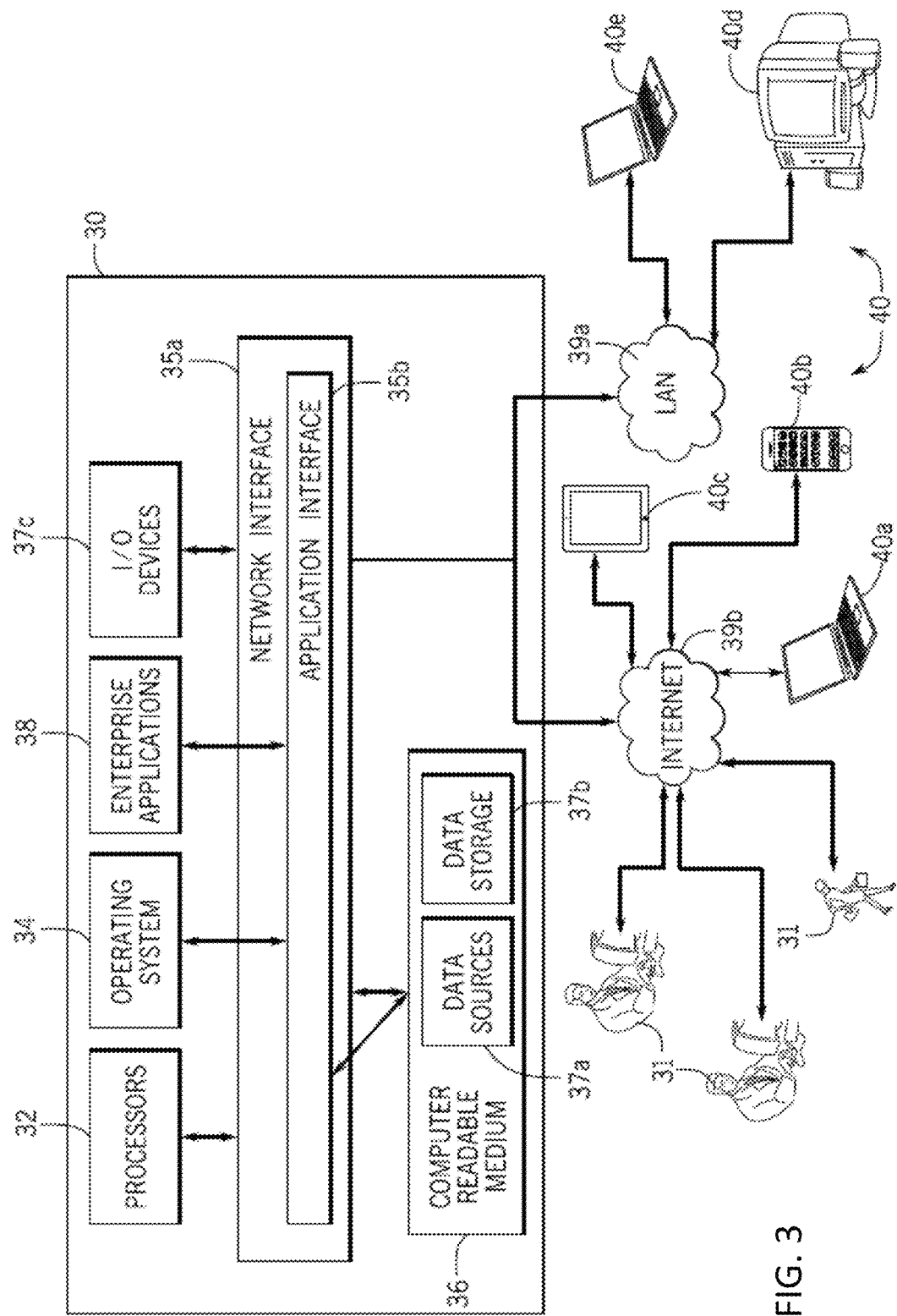
FIG. 3 illustrates a computer system useful for controlling and/or networking to a dental laser station and/or for operating or forming part of the example system of FIG. 1 in accordance with some embodiments of the invention.

FIG. 3 illustrates a computer system 30 useful for controlling and/or networking to a dental laser station (e.g., the dental laser station 200) and/or for operating or forming part of the example system 100 of FIG. 1 in accordance with some embodiments of the invention. In some embodiments, the computer system 30 can control one or more displays (e.g., display 250) for controlling a dental laser station in accordance with some embodiments of the invention. In some embodiments of the invention, the computer system 30 can comprise operating and processing modules of a dental laser station control system and method for a display with a user interface to enable a user to control one or more dental laser stations (e.g., such as dental laser station 200). In some embodiments, the computer system 30 can process one or more software modules of the aforementioned dentistry control system and method, and display information related to dental devices within one or more user interfaces. Further, in some embodiments, using the computer system 30, the dentistry control system and method can manage the organization of data and data flow between the various components of the dentistry control system and method.

In some embodiments, the system 30 can include at least one computing device including one or more processors 32. Some processors 32 can include processors residing in one or more conventional server platforms including within a cloud of computing resources. In some embodiments, the system 30 can include a network interface 35a and/or an application interface 35b coupled to at least one processor 32 capable of running at least one operating system 34. Further, in some embodiments, the at least one processor 32 can be capable of running one or more of the software modules (e.g., such as enterprise applications 38).

Some embodiments include the system 30 comprising at least one computer readable medium 36 coupled to at least one data storage device 37b, and/or at least one data source 37a, and/or at least one input/output device 37c. In some embodiments, the computer readable medium 36 can be any data storage device that can store data, which can thereafter be read by a computer system (such as the system 30). Examples of the computer readable medium 36 can include hard drives, network attached storage (NAS), read-only memory, random-access memory, FLASH based memory, CD-ROMs, CD-Rs, CD-RWs, DVDs, magnetic tapes, other optical and non-optical data storage devices, or any other physical or material medium which can be used to tangibly store the desired information or data or instructions and which can be accessed by a computer or processor (including processors 32).

Some embodiments include a dentistry control system and method embodied as computer readable code on the computer readable medium 36. In some embodiments of the invention, the computer readable medium 36 can also be distributed over a conventional computer network via the network interface 35a so that the computer readable code can be stored and executed in a distributed fashion. For example, in some embodiments, one or more components of the system 30 can be tethered to send and/or receive data through a local area network ("LAN") 39a. In some further embodiments, one or more components of the system 30 can be tethered to send or receive data through an internet 39b (e.g., a wireless internet). Further, in some embodiments, at least one software application 38 running on one or more processors 32 can be configured to be coupled for communication over a network 39a, 39b. In some embodiments, one or more components of the network 39a, 39b can include one or more resources for data storage, including any other form of computer readable media beyond the media 36 for storing information and including any form of computer readable media for communicating information from one electronic device to another electronic device.

In some embodiments, the network 39a, 39b can include wide area networks ("WAN"), direct connections (e.g., through a universal serial bus port) or other forms of computer-readable media 36, or any combination thereof. Further, in some embodiments, one or more components of the network 39a, 39b can include a number of client devices which can be one or more computers 40 including for example desktop computers 40d, laptop computers 40a, 40e, digital assistants and/or personal digital assistants (shown as 40c), cellular phones or mobile phones or smart phones (shown as 40b), pagers, digital tablets, internet appliances, and other processor-based devices. In some embodiments, the computers 40 can include the display 250. In general, a client device can be any type of external or internal devices such as a conventional mouse, CD-ROM, DVD, keyboard, display, or other input or output devices 37c. In some embodiments, various other forms of computer-readable media 36 can transmit or carry instructions to one or more computers 40, including a router, private or public network, or other transmission device or channel, both wired and wireless. In some embodiments, the software modules 38 can be configured to send and receive data from a database (e.g., from a computer readable medium 36 including data sources 37a and data storage 37b that can comprise a database), and data can be received by the software modules 38 from at least one other source.

In some embodiments, at least one of the software modules 38 can be configured within the system 30 to output data to at least one user 31 via at least one digital display (e.g., to a computer 40 comprising a digital display). Further, in some embodiments, the digital display of the computer 40 can include the display 250 of the dental laser station 200 depicted in FIG. 2. In some embodiments, the system 30 as described can enable one or more users 31 to receive, analyze, input, modify, create and send data to and from the system 30, including to and from one or more enterprise applications 38 running on the system 30. Some embodiments include at least one user 31 coupled to a computer 40 accessing one or more modules of the dentistry control system including at least one enterprise applications 38 via a stationary I/O device 37c through a LAN 39a. In some other embodiments, the system 30 can enable at least one user 31 (through computer 40) accessing enterprise applications 38 via a stationary or mobile I/O device 37c through an internet 39a. In some embodiments, the software modules 38 can include a server-based software platform that can include dentistry control software modules suitable for hosting at least one user 31 account and/or at least one patient account or record. In some embodiments, using the system 30, the dentistry control system and method can manage multiple user accounts and/or multiple patient accounts.

Referring to FIG. 1, in some embodiments, the controller 108 can generate or control the GUI 106 with variations based on the operational mode of the dental laser station 200 and/or based at least in part on the status of at least one function of the dental laser station 200, and/or based at least in part on input from the user. In some embodiments of the invention, the controller 108 can include the GUI 106 with various different and customizable controls to enable a user to operate or monitor one or more functions of a dental laser station (e.g., such as dental laser station 200). For example, in some embodiments of the invention, with the display 250 controlled by the system 100, and housed or coupled to one or more control and/or monitoring tools interfaced with the dental laser station 200, a user can interact with any variation of the GUI 106 to control and/or monitor one or more features of the dental laser station 200. For example, in some embodiments, the controller 108 can generate a menu that can comprise one or more features that can be selected, moved, pressed, or otherwise activated by the user. In some other embodiments, one or more features of a menu can be selected or actioned using one or more gestures.

Figure 4:
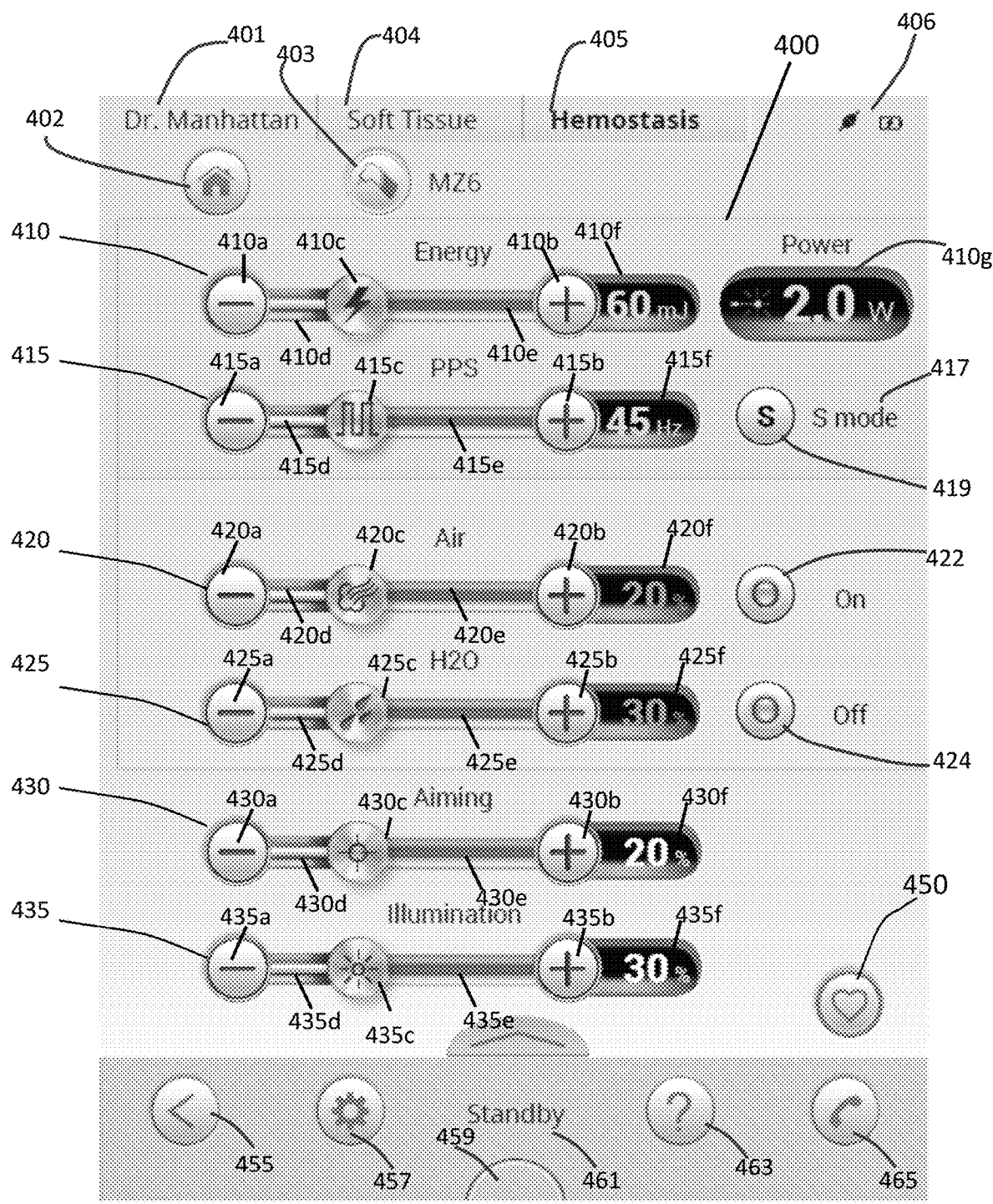
FIG. 4 illustrates an example GUI of the system of FIG. 1 in accordance with some embodiments of the invention.

Referring to FIG. 4, illustrating an example GUI 400 of the system 100 of FIG. 1, some embodiments can include one or more rendered features that comprise one or more user-selectable sliders (or equivalent graphically rendered features). Some alternative embodiments can include other conventional rendered features including, but not limited to, a button, picture or image, icon text, or a combination thereof. In some embodiments, any of the aforementioned rendered features can be animated. In some embodiments, any operational procedure or process of the system 100 aimed at selecting or modifying operational variables, attributes, or functions can be operated through a menu of the GUI 400 that can allow a user to interactively modify the menu, including, for example, to add or subtract category buttons, to modify attribute values, and/or to allow personification of a specific user's (e.g., doctor's) preference system.

Some embodiments can include one or more adjustable parameters that can include, but not be limited to, laser pulse peak power, laser pulse repetition rate, laser pulse duration, laser average output power, and volume and quality of the cooling water spray or air flow (or other fluid delivery). For example, in some embodiments, the GUI 400 can include sliders 410, that can be manipulated by a user to adjust the power of at least one laser source. In other embodiments, the GUI 400 can include sliders 410 that can be manipulated by a user to adjust the pulse rate of at least one laser source. In some further embodiments, other sliders can include, but not be limited to, a slider for user control of air (marked as 420), a slider for user control of water (marked as 425), a slider for user control of aiming (marked as 430), and a slider for user control of illumination (marked as 435). In some other embodiments, the GUI 400 can include one or more numeric displays representing one or more operational parameters (e.g., such as laser power, pulse frequency, percentages of air and water, and percentages of aim and illumination). In some embodiments of the invention, the user can operate one or more of the sliders 410, 415, 420, 425, 430, 435 individually or sequentially. In some embodiments of the invention, the user can adjust two or more sliders at substantially the same rate or at a different or variable rates. In some embodiments of the invention, the user can operate a plurality of the sliders 410, 415, 420, 425, 430, 435 substantially simultaneously.

In some embodiments, the slider 410 can comprise a bar 410e representing a range of selectable values of energy between negative icon end 410a and positive icon end 410b. In some embodiments, the icon 410c can be selected by a user and moved on the bar 410e to any position between the range of selectable values of energy between the negative icon end 410a and the positive icon end 410b. In some embodiments, the bar 410e can include a segment 410d that is illustrative of a selected range of energy based at least in part on the position of the icon 410c on the bar 410e. In some embodiments, the segment 410d can increase in size as the user moves the icon 410c away from the negative icon end 410a and towards the positive icon end 410b, and reduce in size as the icon 410c is moved in the opposite direction towards the negative icon end 410a. In some embodiments, an energy level display 410f can be rendered to provide a user with a numeric illustration of the energy level. In some embodiments, the energy level display 410f can change in real time as the icon 410c is moved along the bar 410e. In some embodiments, a power level display 410g can be rendered to provide a user with a numeric illustration of the power level.

In some embodiments, the slider 415 can comprise a bar 415e representing a range of selectable values of pulse rate between negative icon end 415a and positive icon end 415b. In some embodiments, the icon 415c can be selected by a user and moved on the bar 415e to any position between the range of selectable values of pulse rate between the negative icon end 415a and the positive icon end 415b. In some embodiments, the bar 415e can include a segment 415d that is illustrative of a selected range of pulse rate based at least in part on the position of the icon 415c on the bar 415e. In some embodiments, the segment 415d can increase in size as the user moves the icon 415c away from the negative icon end 415a and towards the positive icon end 415b, and reduce in size as the icon 415c is moved in the opposite direction towards the negative icon end 415a. In some embodiments, an pulse rate level display 415f can be rendered to provide a user with a numeric illustration of the pulse rate level. In some embodiments, the pulse rate level display 415f can change in real time as the icon 415c is moved along the bar 415e. In some embodiments, an "S mode" button 417 can be rendered to provide a user selectable S-mode of a laser of the system 100. In some embodiments, the user can select the icon end 415a or icon end 415b to move the slider 415c on the bar 415e. For example, in some embodiments, a user selection of the icon end 415a can result in the movement of the icon 415c towards the icon end 415a, and a user selection of the icon end 415b can result in the movement of the icon 415c towards the icon end 415b.

In some embodiments, the slider 420 can comprise a bar 420e representing a range of selectable values of air between negative icon end 420a and positive icon end 420b. In some embodiments, the icon 420c can be selected by a user and moved on the bar 420e to any position between the range of selectable values of air between the negative icon end 420a and the positive icon end 420b. In some embodiments, the bar 420e can include a segment 420d that is illustrative of a selected range of air based at least in part on the position of the icon 420c on the bar 420e. In some embodiments, the segment 420d can increase in size as the user moves the icon 420c away from the negative icon end 420a and towards the positive icon end 420b, and reduce in size as the icon 420c is moved in the opposite direction towards the negative icon end 420a. In some embodiments, an air level display 420f can be rendered to provide a user with a numeric illustration of the air level. In some embodiments, the air level display 420f can change in real time as the icon 420c is moved along the bar 420e. Some embodiments include an on and off button 422, 424 to enable a user to control fluid delivery. In some embodiments, the user can select the icon end 420a or icon end 420b to move the slider 420c on the bar 420e. For example, in some embodiments, a user selection of the icon end 420a can result in the movement of the icon 420c towards the icon end 420a, and a user selection of the icon end 420b can result in the movement of the icon 420c towards the icon end 420b.

In some embodiments, the slider 425 can comprise a bar 425e representing a range of selectable values of water between negative icon end 425a and positive icon end 425b. In some embodiments, the icon 425c can be selected by a user and moved on the bar 425e to any position between the range of selectable values of water between the negative icon end 425a and the positive icon end 425b. In some embodiments, the bar 425e can include a segment 425d that is illustrative of a selected range of water based at least in part on the position of the icon 425c on the bar 425e. In some embodiments, the segment 425d can increase in size as the user moves the icon 425c away from the negative icon end 425a and towards the positive icon end 425b, and reduce in size as the icon 425c is moved in the opposite direction towards the negative icon end 425a. In some embodiments, an water level display 425f can be rendered to provide a user with a numeric illustration of the water level. In some embodiments, the water level display 425f can change in real time as the icon 425c is moved along the bar 425e. In some embodiments, the user can select the icon end 425a or icon end 425b to move the slider 425c on the bar 425e. For example, in some embodiments, a user selection of the icon end 425a can result in the movement of the icon 425c towards the icon end 425a, and a user selection of the icon end 425b can result in the movement of the icon 425c towards the icon end 425b.

In some embodiments, the slider 430 can comprise a bar 430e representing a range of selectable values of aiming between negative icon end 430a and positive icon end 430b. In some embodiments, the icon 430c can be selected by a user and moved on the bar 430e to any position between the range of selectable values of aiming between the negative icon end 430a and the positive icon end 430b. In some embodiments, the bar 430e can include a segment 430d that is illustrative of a selected range of aiming based at least in part on the position of the icon 430c on the bar 430e. In some embodiments, the segment 430d can increase in size as the user moves the icon 430c away from the negative icon end 430a and towards the positive icon end 430b, and reduce in size as the icon 430c is moved in the opposite direction towards the negative icon end 430a. In some embodiments, an aiming level display 430f can be rendered to provide a user with a numeric illustration of the aiming level. In some embodiments, the aiming level display 430f can change in real time as the icon 430c is moved along the bar 430e. In some embodiments, the user can select the icon end 430a or icon end 430b to move the slider 430c on the bar 430e. For example, in some embodiments, a user selection of the icon end 430a can result in the movement of the icon 430c towards the icon end 430a, and a user selection of the icon end 430b can result in the movement of the icon 430c towards the icon end 430b.

In some embodiments, the slider 435 can comprise a bar 435e representing a range of selectable values of illumination between negative icon end 435a and positive icon end 435b. In some embodiments, the icon 435c can be selected by a user and moved on the bar 435e to any position between the range of selectable values of illumination between the negative icon end 435a and the positive icon end 435b. In some embodiments, the bar 435e can include a segment 435d that is illustrative of a selected range of illumination based at least in part on the position of the icon 435c on the bar 435e. In some embodiments, the segment 435d can increase in size as the user moves the icon 435c away from the negative icon end 435a and towards the positive icon end 435b, and reduce in size as the icon 435c is moved in the opposite direction towards the negative icon end 435a. In some embodiments, an illumination level display 435f can be rendered to provide a user with a numeric illustration of the illumination level. In some embodiments, the illumination level display 435f can change in real time as the icon 435c is moved along the bar 435e. In some embodiments, the user can select the icon end 435a or icon end 435b to move the slider 435c on the bar 435e. For example, in some embodiments, a user selection of the icon end 435a can result in the movement of the icon 435c towards the icon end 435a, and a user selection of the icon end 435b can result in the movement of the icon 435c towards the icon end 435b.

In some embodiments, one or more parameters of a dental laser station (e.g., such as dental laser station 200) can be controlled with a single control button or slider and any change in values can be accordingly reflected a control panel of a GUI (e.g., such as illustrated in GUI 400). In some embodiments, any one or more of the parameters discussed above with respect to sliders 410, 415, 420, 425, 430, and 435 can be controlled using a single slider. Additionally, in some embodiments, a user (e.g., such as a dentist or doctor) can save an adjusted set of system parameters as a preferred setting for use at any other time. In some embodiments, the GUI 400 can be configured using the controller 108 to enable a user to operate more than one of the sliders 410, 415, 420, 425, 430, 435 using a single slider, button, toggle, gesture, or any other conventional input as described earlier. For example, in some embodiments, a single or master control knob or slider can be used to simultaneously adjust two or system parameters to maintain safety and effectiveness of system operation. In some embodiments, all parameters can be shown simultaneously within a control terminal GUI display, and adjustment of one knob (or slider) can show the change of more than one of the system parameters. For example, in some embodiments, either one of the sliders 410, 415 for adjusting the power and pulse of at least one laser source can be adjusted by the user, while the controller 108 can automatically adjust at least one of the other sliders for control of air (420), water (425), aiming (430), and/or illumination (435). In some other embodiments, adjustment of the slider 410 can force automatic adjustment of the slider 415, and any one or more of the sliders 420, 425, 430, 435. In some further embodiments, adjustment of the slider 415 can force automatic (or semiautomatic) adjustment of the slider 410, and any one or more of the sliders 420, 425, 430, 435. In some further embodiments of the invention, at least one additional control feature (e.g., a button, slider, toggle, or other user-selectable feature) can be included in the GUI 400 that can be used by the user to adjust one or more of the sliders 410, 415, 420, 425, 430, 435. In some embodiments, the additional control feature can be used to control, substantially simultaneously, at least two or more of the sliders 410, 415, 420, 425, 430, 435.

In some embodiments, the controller 108 can provide automatic adjustments as described above that occur at substantially the same time and/or substantially the same rate as the user adjusted slider. For example, in reference to the non-limiting example above, in some embodiments, if a user adjusts slider 410 at a specific rate, any one or more of the sliders 415, 420, 425, 430, 435 can move at the same rate and at substantially the same time. In some other embodiments, any one or more of the sliders 415, 420, 425, 430, 435 can move at a different or variable rate than the adjustment rate of the slider 410. Further, when at least one other additional control feature (e.g., a button, slider, toggle, or other user-selectable feature) is included in the GUI 400, the controller 108 can adjust one or more of the sliders 410, 415, 420, 425, 430, 435 at substantially the same specific rate applied by the user to the additional control feature. In some embodiments, the additional control feature can be used to control, substantially simultaneously, at least two or more of the sliders 410, 415, 420, 425, 430, 435. For example, if a user adjusts the additional control feature at a specific rate, any one or more of the sliders 415, 420, 425, 430, 435 can move at the same rate and at substantially the same time. In some other embodiments, any one or more of the sliders 415, 420, 425, 430, 435 can move at a different or variable rate than the adjustment rate of the additional control feature.

In some embodiments, a user can assign or select one or more control parameters and/or one or more preferences using any of the user-selectable or adjustable features, controls, or processes described herein. For example, in some embodiments, any procedure operated through a menu of the GUI 400 can be selected or assigned for a specific user's preference system. Some embodiments include methods to alter and create original clinical protocols for advanced practitioners after being certified and allowed to do so by manufacturers (e.g., where verification of modified and new protocols is performed by the manufacturer for safety and effectiveness as well as compliance with current FDA clearance for clinical applications and indications for use). In some embodiments, advanced users can eliminate, create new, and re-position steps within any one or more particular procedures. In some embodiments, the user can select separate steps from different clinical applications and combine them together creating a modified or new clinical application. For example, a step or steps can form any specific dental procedure and/or can be from any specific dental specialty including, but not limited to general dentistry, oral and maxillofacial dentistry, orthodontic dentistry, endodontic dentistry, pediatric dentistry, cosmetic dentistry, and so on. In some embodiments, a user can be enabled by the system 100 to develop an original application from the beginning and not based on any particular procedure as a reference. For example, in some embodiments, icon or button 450 can be used to select or assign one or more adjustable parameters including, but not limited to laser pulse peak power, laser pulse repetition rate, laser pulse duration, laser average output power, and volume and quality of the cooling water spray or air flow.

Some embodiments of the GUI 400 of the system 100 can include one or more operational or functional representation, alerts or status of a coupled dental system. For example, in some embodiments, the GUI 400 can comprise a home button 402 to enable a user to select or revert to a homepage or window. In some embodiments, the GUI 400 can include one or more selectable and/or overlapping or underlying windows or menus. For example, some embodiments include a top window or menu 401 with other selectable windows 404, 405 being selectable and/or configurable by selection. In some embodiments, the GUI 400 can include a display of the power and/or battery status of a coupled dental system. For example, some embodiments include power and/or battery status 406. Some embodiments include other controls or selectable features including a back selector 455, option or controls selector 457, a help icon 463, and/or a phone or communicate icon 465. Some embodiments include a help icon and/or other customer service access icon or menu. For example, some embodiments include the help icon 463 and/or other customer service access icon or menu on the GUI 400 can enable a user to access customer service. Some embodiments include other learning access icons or menus that can enable customer service access with a single touch of the GUI 400. In some embodiments, the icon 465 and/or other service access icon or menu on the GUI 400 can enable a user to obtain clinical, technical or business assistance. In some embodiments, the icon 465 can enable clinical, technical or business assistance with a single touch of the GUI 400.

In some embodiments, a status of a coupled dental laser can be shown on the GUI 400. For example, some embodiments include a display line 461 that can represent "standby" and/or an icon 459 that can include a graphical element indicating the "standby" mode (e.g., the icon 459 can comprise a representative color such as yellow). In some embodiments, a coupled dental laser can be turned off or on using the GUI 400. For example, some embodiments include an off icon 424 and an on icon 422. In some further embodiments, a mode of a coupled dental laser can be shown and/or selected. For example, some embodiments include a mode line 417 and/or a mode icon 419. Some embodiments include a handpiece or tool selector icon 403.

Figure 5:
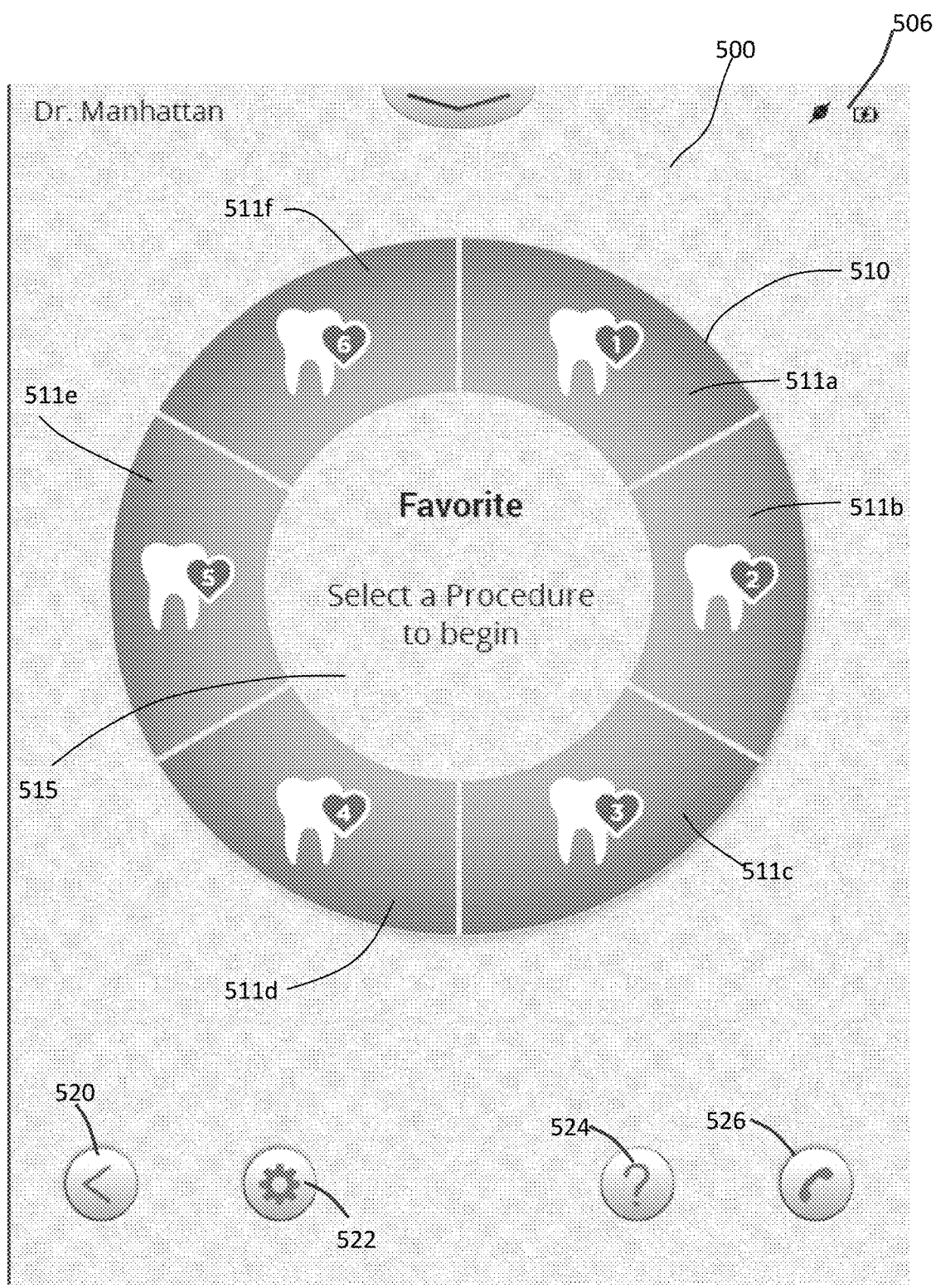
FIG. 5 illustrates a GUI including a favorites selector wheel in accordance with some embodiments of the invention.

In some embodiments, any of sliders 410, 415 for adjusting the power and pulse of at least one laser source, and/or sliders for control of air (marked as 420), water (marked as 425), aiming (marked as 430), and illumination (marked as 435) can be adjusted by a user and stored as a favorite using the icon or button 450. In some embodiments, a user can adjust a single slider and mark the adjusted setting as a favorite setting. In some further embodiments, the user can adjust multiple sliders and mark them as one or more favorite settings. In some embodiments of the invention, one or more favorite settings can be selected or recalled using a favorite selector. For example, FIG. 5 illustrates a GUI 500 including a favorites selector wheel 510 in accordance with some embodiments of the invention. In some embodiments, using the GUI 500, a user can adjust parameters for a particular clinical application including specific dental procedure and/or for any specific dental specialty including, but not limited to general dentistry, oral and maxillofacial dentistry, orthodontic dentistry, endodontic dentistry, pediatric dentistry, cosmetic dentistry, and so on. For example, in some embodiments, a user can choose one or more selected or assigned favorites, where the favorites can include, but not be limited to, guidelines from manufacturer, guidelines from a particular educational program, settings or guidelines from a user's experience and education, one or more pre-sets or pre-programmed sets of parameters, one or more complex procedures comprising step-by-step pre-programmed settings with certain names and performance guidelines, or a combination thereof. In some embodiments, the selected or assigned favorites can include one or more adjustable parameters including, but not limited to laser pulse peak power, laser pulse repetition rate, laser pulse duration, laser average output power, and volume and quality of the cooling water spray or air flow that were previously assigned or selected using icon or button 450 using the procedures detailed above.

In some embodiments, one or more operating or functional parameters of a dental laser station (e.g., such as dental laser station 200) can be selected or assigned using the GUI 500 through the favorites selector wheel 510. For example, in some embodiments, any one or more of the favorite segments 511a, 511b, 511c, 511d, 511e, 511f can be assigned or selected as one or more favorites comprising of one or more variables, parameters or guidelines, including, but limited to, guidelines from a manufacturer, guidelines from a particular educational program, settings or guidelines from a user's experience and education, one or more pre-sets or pre-programmed sets of parameters, one or more complex procedures comprising step-by-step pre-programmed settings with certain names and performance guidelines, or a combination thereof. In some embodiments, the more variables, parameters or guidelines can include one or more adjustable parameters including, but not limited to laser pulse peak power, laser pulse repetition rate, laser pulse duration, laser average output power, and volume and quality of the cooling water spray or air flow that were previously assigned or selected using icon or button 450 using the procedures detailed above.

In some embodiments, the favorites selector wheel 510 can be used to select a single favorite variable, parameter or guideline. In some other embodiments, the favorites selector wheel 510 can be used to select more than one favorite variable, parameter or guideline. In some embodiments, the user can use the favorites selector wheel 510 to select a series of favorite variables, parameters or guidelines. In some embodiments, the favorites selector wheel 510 can enable the user to select a series of favorite variables, parameters or guidelines in a specific order defining one or more clinical protocols, and in doing so, can select or assign specific dental procedures and/or for any specific dental specialty including, but not limited to general dentistry, oral and maxillofacial dentistry, orthodontic dentistry, endodontic dentistry, pediatric dentistry, cosmetic dentistry, and so on.

Some embodiments include other controls or selectable features including a back selector 520, option or controls selector 522, a help icon 524, and/or a phone or communicate icon 526. Some embodiments include a help icon and/or other customer service access icon or menu. For example, some embodiments include the help icon 524 and/or other customer service access icon or menu on the GUI 500 can enable a user to access customer service. Some embodiments include other learning access icons or menus that can enable customer service access with a single touch of the GUI 500. In some embodiments, the icon 526 and/or other service access icon or menu on the GUI 500 can enable a user to obtain clinical, technical or business assistance. In some embodiments, the icon 526 can enable clinical, technical or business assistance with a single touch of the GUI 500.

In some embodiments of the invention, dental laser control and/or monitoring parameters can be displayed in a GUI in the form of a circular pie chart or in the form of at least one conventional drop down menu. In some embodiments, this type of GUI can be used with a laser system or in combination with other systems. For example, in some embodiments, the GUI 600 of FIG. 6 can be used to control a dental laser station such as the dental laser station 200 shown in FIG. 2. In some embodiments, the GUI 600 can include a control wheel 605 comprising a plurality of segments 608. In some embodiments, the segments 608 can comprise a single segment. In other embodiments, the segments 608 can comprise multiple segments (shown as selected or active segment 610, and segments 611a, 611b, 611c, 611d, and 611e) that can be used to select specific programs, operating parameters, and/or procedures. For example, in some embodiments, segment 610 can represent specific programs, operating parameters, and/or procedures for "outer de-epi". Further, in some embodiments, segment 611a can represent specific programs, operating parameters, and/or procedures for "GV". Further, in some embodiments, segment 611b can represent specific programs, operating parameters, and/or procedures for "retraction". Further, in some embodiments, segment 611c can represent specific programs, operating parameters, and/or procedures for "degranulation". Further, in some embodiments, segment 611d can represent specific programs, operating parameters, and/or procedures for "decort". Further, in some embodiments, segment 611e can represent specific programs, operating parameters, and/or procedures for "final debridement".

In some embodiments, the control wheel 605 can be used to control and communicate one or more functions or operational parameters of the dental laser station 200. Some embodiments include various function readouts or meters associated within one or more operational parameters of a dental laser station. For example, in some embodiments, the control wheel 605 can include a central display 620 at least partially surrounded by the segments described above (e.g., selected or active segment 610, and segments 611a, 611b, 611c, 611d, and 611e). In some further embodiments, the central display 620 can display information related to one or more functions and/or operating parameters of the dental laser station 200. In some embodiments, any one of the segments can be actuatable by a user. For example, in some embodiments, any one of the segments can be selected by a user through a user interaction with the GUI 600 (e.g., using any of the user interactions or actions described earlier).

Figure 6:
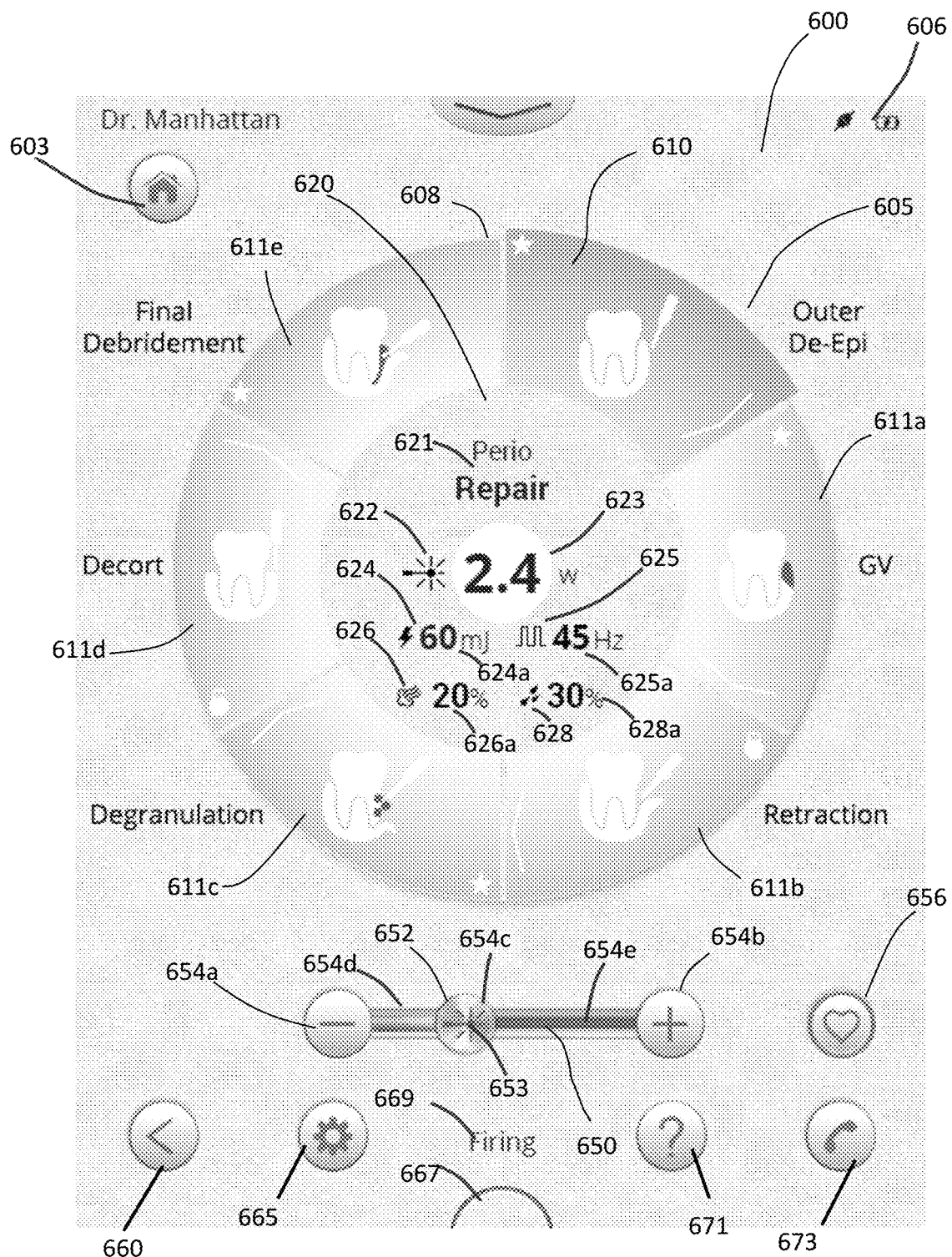
FIG. 6 illustrates a GUI including a master control in accordance with some embodiments of the invention.

In some embodiments, any of the segments described above can include a visual icon comprising a banner, graphic, image, text, or combinations thereof. In some embodiments, the visual icon can comprise a notification or description of the underlying segment. In some embodiments, following a user selection of a specific segment, the contents of a variation of the contents of the visual icon of the chosen segment can be displayed in the central display 620. Further, in some embodiments, the segment can be identified as being selected (e.g., such as shown in the example embodiments. For example, in the non-limiting embodiments shown, the segment includes a distinguishing graphical look (where the segment 610 is shown separated from adjacent segments). In other embodiments, the selected segment can be distinguished by color, shape, size, animation, or any other conventional GUI display format, and/or any combination thereof. One of ordinary skill in the art that FIG. 6 is shown with active segment 610 for illustrative purposes can that the control wheel 605 can in include more selected segments with the appearance the same or similar to active segment 610, or with no active segments.

In some embodiments, any procedure operated through the control wheel 605 of the GUI 600 can enable a user to update, select, or modify the control wheel 605, including, for example, to add or subtract category segments or buttons, to modify attribute values, and/or to allow personification of a specific doctor's preference system. In some embodiments, the adjustable parameters can include, but not be limited to, laser pulse peak power, laser pulse repetition rate, laser pulse duration, laser average output power, and volume and quality of the cooling water spray or air flow. For example, in some embodiments, the GUI 600 can include adjustable parameters for the power and pulse of at least one laser source. In some further embodiments, other adjustable parameters for control of air, water, aiming, and illumination, or other adjustable parameters can also be included. In some embodiments, the GUI 600 can also include one or more numeric displays representing operational parameters (e.g., such as laser power, pulse frequency, percentages of air and water, and percentages of aim and illumination) with and/or adjacent to the central display 620.

In some embodiments, the user can use the GUI 600 to change or modify one or more parameters related to the operation and function of a dental laser, including, but not limited to, laser pulse peak power, laser pulse repetition rate, laser pulse duration, laser average output power, and volume and quality of the cooling water spray or air flow. In some embodiments, this can be achieved using a master control 650. For example, in some embodiments, using the master control 650, any of the parameters that would normally be controlled by the one or more of the sliders 410, 415, 420, 425, 430, 435 of the GUI 400 of FIG. 4, can be modified substantially simultaneously using the master control 650. In some embodiments, parameters of a dental laser station (e.g., such as dental laser station 200) can be controlled using the master control 650, and any change in values can accordingly be reflected in the GUI (e.g., such as within the central display 620.) In some embodiments, the master control 650 can comprise a slider 652 that can be moved by the user when adjusting the master control 650. Further, in some embodiments, the master control 650 can include increment buttons 654a, 654b that a user can select for incremental movement of the slider 652. In some embodiments, the slider 652 can comprise a bar 654e representing a range between negative end button (increment button 654a) and positive end (shown as increment button 654b). In some embodiments, the icon 654c can be selected by a user and moved on the bar 654e to any position between the range of selectable values between negative end button (increment button 654a) and positive end (shown as increment button 654b). In some embodiments, the bar 654e can include a segment 654d that is illustrative of a selected range based at least in part on the position of the icon 654c on the bar 654e. In some embodiments, the segment 654d can increase in size as the user moves the icon 654c away from the negative end button (button 654a) towards the positive end (button 654b), and reduce in size as the icon 654c is moved in the opposite direction towards the negative end button. In some embodiments, the user can select the button 654a or button 654b to move the slider 652 on the bar 654e. For example, in some embodiments, a user selection of the button 654a can result in the movement of the icon 654c towards the button 654a, and a user selection of the button 654b can result in the movement of the icon 654c towards the button 654b.

In some embodiments, a user-selectable controller of the master control 650 can include a representation of one or more parameters related to the operation and function of a dental laser, including, but not limited to, laser pulse peak power, laser pulse repetition rate, laser pulse duration, laser average output power, and volume and quality of the cooling water spray or air flow. For example, as shown in the non-limiting embodiment of FIG. 6, some embodiments include the icon 654c that includes laser icon 653. In some embodiments, this icon can change based on the selected procedure and/or the one or more parameters being controlled by the master control 650.

In some embodiments, the parameters of a dental laser station (e.g., such as dental laser station 200) can be displayed as representative values, icons, graphics, and/or text in the GUI (e.g., such as within the central display 620). For example, as shown in the non-limiting embodiment of FIG. 6, some embodiments include a displayed procedure name 621. Further, some embodiments include a laser status icon 622 illustrative of a status of one or more laser sources 103. Some embodiments also include a power level display 623 illustrative of the current power level of the one or more laser sources 103. Some further embodiments include an energy level icon 624 that in some embodiments includes an adjacent energy level display 624a showing a display of the energy level. Some further embodiments include an air level icon 626 that in some embodiments includes an adjacent air level display 626a showing a display of the air flow level. Some further embodiments include a water level icon 628 that in some embodiments includes an adjacent water level display 628a showing a display of the water flow level. Some further embodiments include a frequency level icon 625 that in some embodiments includes an adjacent frequency level display 625a showing a display of the frequency level.

In some embodiments, the GUI 600 can be configured using the controller 108 to enable a user to operate more than one of the parameters or functions represented by the sliders 410, 415, 420, 425, 430, 435 using a single slider (as depicted with master control 650), button, toggle, gesture, or any other conventional input as described earlier. For example, in some embodiments, the master control 650 can be used to simultaneously adjust two or more system parameters to maintain safety and effectiveness of system operation of a dental laser station 200. In some embodiments, the master control 650 can be used for adjusting the power and pulse of at least one laser source (e.g., such as the power and pulse represented by sliders 410, 415), while the controller 108 can automatically (or semi-automatically) adjust at least one other parameter such as air, water, aiming, and/or illumination (e.g., the parameters or functions represented by the sliders 410, 415, 420, 425, 430, 435 shown in FIG. 4). In some embodiments, the GUI 600 can include sliders 410, 415, 420, 425, 430, 435 that can be updated by the controller 108 as the master controller 650 is accessed and input is received by the user. In some further embodiments of the invention, an additional control feature (e.g., a button, slider, toggle, or other user-selectable feature) can be included in the GUI 600 that can be used by the user to adjust one or more additional parameters or functions represented by the sliders 410, 415, 420, 425, 430, 435. In some embodiments, the additional control feature and/or the master control 650 can be used to control, substantially simultaneously, at least two or more of the parameters or functions represented by the sliders 410, 415, 420, 425, 430, 435, or other conventional control and operational parameters of a dental laser.

In some embodiments, the controller 108 can provide adjustments that occur at substantially the same time and/or substantially the same rate as the master control 650. For example, in some embodiments, if a user adjusts the master control 650 at a specific rate, any one or more of the parameters or functions represented by the sliders 410, 415, 420, 425, 430, 435 as described earlier can adjust at the same rate and at substantially the same time. In some other embodiments, any one or more of parameters or functions represented by the sliders 410, 415, 420, 425, 430, 435 can adjust at a different or variable rate than the adjustment rate of the master control 650. Further, in some embodiments of the invention, when at least one other additional control feature (e.g., a button, slider, toggle, or other user-selectable feature) is included in the GUI 600, the controller 108 can adjust one or more of the parameters or functions represented by the sliders 410, 415, 420, 425, 430, 435 at substantially the same specific rate applied by the user to the additional control feature and/or to the master control 650. In some embodiments, at least one other additional control feature can be used to substantially simultaneously control at least two or more of the parameters or functions represented by the sliders 410, 415, 420, 425, 430, 435. For example, in some embodiments, if a user adjusts the additional control feature at a specific rate, any of the parameters or functions represented by the one or more of the sliders 415, 420, 425, 430, 435 can move at the same rate and/or at substantially the same time. In some other embodiments, any one or more of the parameters or functions represented by the sliders 415, 420, 425, 430, 435 can move at a different or variable rate than the adjustment rate of the additional control feature.

In some embodiments, the user (e.g., such as a dentist or doctor) can save an adjusted set of system parameters as a preferred or favorite setting for use at any other time (e.g., using button or icon 656). For example, in some embodiments, any of the settings or parameters defined by any one or more of the user interactions and protocols discussed above with respect to the GUI 600 can be assigned to one or more favorites and/or selected from one or more favorites. For example, in some embodiments, any parameters, variables, settings or guidelines from GUI 600 can be assigned any one or more of the favorite segments 511a, 511b, 511c, 511d, 511e, 511f of the favorites selector wheel 510. Further, in some embodiments, any parameters, variables, settings or guidelines defined by a user using GUI 600 can be selected from any one or more of the favorite segments 511a, 511b, 511c, 511d, 511e, 511f of the favorites selector wheel 510. For example, in some embodiments, any one or more of the favorite segments 511a, 511b, 511c, 511d, 511e, 511f can be selected to control a dental laser station such as the dental laser station 200 shown in FIG. 2.

In some embodiments any one of the segments 608 including any one or more of the segments 611a, 611b, 611c, 611d, and 611e can be used to select specific programs, operating parameters, and/or procedures through assignment of one or more favorites using any one or more of the favorite segments 511a, 511b, 511c, 511d, 511e, 511f of the favorites selector wheel 510. For example, specific programs, operating parameters, and/or procedures for "outer de-epi" (segment 610), and/or specific programs, operating parameters, and/or procedures for "GV" (segment 611a), and/or specific programs, operating parameters, and/or procedures for "retraction" (segment 611b), and/or specific programs, operating parameters, and/or procedures for "degranulation" (segment 611c), and/or specific programs, operating parameters, and/or procedures for "decort" (segment 611d), and/or specific programs, operating parameters, and/or procedures for "final debridement" (segment 611e) can be assigned to or from any one of the segments 608 including segments 611a, 611b, 611c, 611d, and 611e. In some embodiments, once selected, the user can assign or select to begin a procedure using the central icon 515.

Some embodiments include other controls or selectable features including a back selector 660, option or controls selector 665, a help icon, and/or a phone or communicate icon 673. Some embodiments include a help icon 671 and/or other customer service access icon or menu. For example, some embodiments include the help icon 671 and/or other customer service access icon or menu on the GUI 600 can enable a user to access customer service. Some embodiments include other learning access icons or menus that can enable customer service access with a single touch of the GUI 600. In some embodiments, the icon 673 and/or other service access icon or menu on the GUI 600 can enable a user to obtain clinical, technical or business assistance. In some embodiments, the icon 673 can enable clinical, technical or business assistance with a single touch of the GUI 600.

In some embodiments of the invention, any of the GUI's described herein can include more or less detail and/or more or less user functions or user interactive elements. For example, in some embodiments, the GUI 400, GUI 500, and/or GUI 600 can be customized based on the expected level of experience of the user. In other embodiments, the GUI's can be customized based on a learned level of experience of the user. In some further embodiments, the GUI's can be customized based on user-selected level of experience of the user. In some embodiments, the GUI's can be customized for a "basic" level. In some further embodiments, the GUI's can be customized for an "advanced" level. In other embodiments, the GUI's can be customized for an "expert" level.

In some embodiments, any of the help icons and/or other learning access icon or menu described can enable a user to view one or more tutorials and/or help or information displays. For example, in some embodiments, the help icon 463 and/or other learning access icon or menu can enable a user to view one or more tutorials and/or help or information displays with a single touch of the GUI 400. In some embodiments, the one or more tutorials and/or help or information displays can include one or more animated tutorials including learning content. For example, some embodiments include tutorials related to restorative procedures, including, but not limited to, cavity preparations, and/or sub-gingival decay removal, and/or troughing. Further for example, some embodiments include tutorials related to soft-tissue procedures, including, but not limited to achieving hemostasis, and/or frenectomy techniques, and/or biopsies and lesions. Further, for example, some embodiments include tutorials related to perio procedures, including, but not limited to repair perio protocol (all steps), closed crown lengthening, and flap surgery. Further, for example, some embodiments include tutorials related to implant procedures including, but not limited to, repair implant protocol (all steps), and/or implant debridement, and/or flap surgery. Further, for example, some embodiments include tutorials related to endo procedures, including, but not limited to, access, cleaning, and shaping, pulpotomy, pulp cap, disinfection of root canal, and/or removal of smear layer.

Some embodiments include a loaded system menu including rich, onboard reference material and other information designed to help users quickly become expert. Some embodiments enable users to access best practices from other users and clinical mentors, how-to videos, and much more at your fingertips. Some embodiments enable users to connect and collaborate with other users. In some embodiments, any of the help icons or other access icons described earlier can enable a user to access a learning center, including, but not limited to, instructional videos, operational videos for the team, and/or business and marketing tips.

In some embodiments, any of the help icons or other access icons described earlier can enable a user to stay up to date online, including, but not limited to, obtaining the latest educational content, being able to view the user's profile and usage statistics, and being able to view and/or update software and settings. In some further embodiments, any of the help icons or other access icons described earlier can enable a user to connect with peers, including, but not limited to, being enabled to learn from fellow owners, and/or share cases and get advice, and/or collaborate for best practices, download new clinical technique videos, and/or use the latest pre-sets from the experts.

With the above embodiments in mind, it should be understood that the invention can employ various computer-implemented operations involving dentistry control data stored in computer systems. Moreover, the above-described databases and models throughout the dentistry control can store analytical models and other data on computer-readable storage media within the system 30 and on computer-readable storage media coupled to the system 30. In addition, the above-described applications of the dentistry control system can be stored on computer-readable storage media within the system 30 and on computer-readable storage media coupled to the system 30. These operations are those requiring physical manipulation of physical quantities. Usually, though not necessarily, these quantities take the form of electrical, electromagnetic, or magnetic signals, optical or magneto-optical form capable of being stored, transferred, combined, compared and otherwise manipulated.

Any of the operations described herein that form part of the invention are useful machine operations. The invention also relates to a device or an apparatus for performing these operations. The apparatus can be specially constructed for the required purpose, such as a special purpose computer. When defined as a special purpose computer, the computer can also perform other processing, program execution or routines that are not part of the special purpose, while still being capable of operating for the special purpose. Alternatively, the operations can be processed by a general purpose computer selectively activated or configured by one or more computer programs stored in the computer memory, cache, or obtained over a network. When data is obtained over a network the data can be processed by other computers on the network, e.g. a cloud of computing resources.

The embodiments of the present invention can also be defined as a machine that transforms data from one state to another state. The data can represent an article, that can be represented as an electronic signal and electronically manipulate data. The transformed data can, in some cases, be visually depicted on a display, representing the physical object that results from the transformation of data. The transformed data can be saved to storage generally or in particular formats that enable the construction or depiction of a physical and tangible object. In some embodiments, the manipulation can be performed by a processor. In such an example, the processor thus transforms the data from one thing to another. Still further, the methods can be processed by one or more machines or processors that can be connected over a network. Each machine can transform data from one state or thing to another, and can also process data, save data to storage, transmit data over a network, display the result, or communicate the result to another machine. Computer-readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data.

Although method operations can be described in a specific order, it should be understood that other housekeeping operations can be performed in between operations, or operations can be adjusted so that they occur at slightly different times, or can be distributed in a system which allows the occurrence of the processing operations at various intervals associated with the processing, as long as the processing of the overlay operations are performed in the desired way.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto.

The invention claimed is:

1. A dental laser system comprising:
   at least one electromagnetic energy source;
   at least one controller coupled to the at least one electromagnetic energy source, the at least one controller coupled to a graphical user interface configured to enable a user to provide input to the at least one controller to control at least one operating parameter of the at least one electromagnetic energy source; and
   wherein under control of the at least one controller, the graphical user interface is configured and arranged to render graphical content;
   wherein the at least one controller is configured and arranged to enable a user to control a plurality of parameters of the dental laser system with a single action or input to the graphical user interface;
   wherein the single action or input from the user involves an interaction with a graphical portion of the at least one controller;
   wherein the interaction controls more than one operational parameter of the dental laser system without a requirement for the user to provide an additional interaction with any other adjacent graphical portion of the graphical user interface; and
   at least one graphic indicative of at least one of a mode, an operational status, and an operational parameter of the dental laser system, wherein the at least one graphic is displayed, updated, or animated by the at least one controller; and
   wherein the at least one controller comprises a single control as the only control displayed on the graphical user interface; and
   wherein interaction of the single control by a user results in the at least one controller updating the operating parameters display of at least one of laser pulse peak power, laser pulse repetition rate, laser pulse duration, laser average output power, while simultaneously updating at least one of air delivery and water delivery.

2. The system of claim 1, wherein the at least one graphic includes at least one icon, textural display, or graphical update that is displayed, updated, or animated by the at least one controller based at least in part on the user's interaction with the graphical portion of the at least one controller.

3. The system of claim 1, wherein the at least one controller comprises a slider.

4. The system of claim 3, wherein the slider comprises at least one of a laser energy control slider, a laser pulse width slider, at least one fluid delivery control slider, an aiming slider, and an illumination slider.

5. The system of claim 3, wherein the at least one controller comprises a single slider as the only slider displayed on the graphical user interface.

6. The system of claim 3, wherein the at least one controller comprises a single slider displayed to the user with at least one other slider displayed elsewhere in the graphical user interface.

7. The system of claim 6, wherein the at least one controller is configured to move the at least one other slider based at least in part on the user's interaction with the graphical portion of the at least one controller.

8. The system of claim 7, wherein the at least one controller is configured to move at least a graphical portion of the at least one other slider at the same rate as the at least one controller moves at least a graphical portion of the at least one controller based at least in part on the user's interaction.

9. The system of claim 7, wherein the at least one controller is configured to move at least a graphical portion of the at least one other slider at a different rate than the at least one controller moves at least a graphical portion of the at least one controller based at least in part on the user's interaction.

10. The system of claim 3, wherein the slider is positioned on a slide bar, the slider being moveable on the slide bar based on user input.

11. The system of claim 10, wherein the user input includes dragging the slider on the slide bar.

12. The system of claim 3, wherein the outer display comprises a circular control wheel including a plurality of segments selectable by a touch of a user.

13. The system of claim 12, wherein the circular control wheel includes a display of treatment categories, treatment procedures or laser control options on at least some of the plurality of segments.

14. The system of claim 12, wherein upon selection of a segment, the at least one controller is configured and arranged to render the segment with a distinguishing graphical look based on the touch of the user.

15. The system of claim 12, further comprising a favorite selection icon providing an option to favorite a procedure and/or step of a procedure.

16. The system of claim 12, wherein the control wheel comprises at least one user-defined or selected favorite dental procedures or favorite steps of a dental procedure represented as at least one of the user-selectable segments.

17. The system of claim 1, wherein the graphical content includes a circular central display at least partially encircled by a rendered circular outer display.

18. The system of claim 17, wherein the central display includes an operating parameters display of laser energy, laser power, a pulse frequency, air delivery, and water delivery.

19. The system of claim 18, wherein the at least one controller comprises a single slider as the only slider displayed on the graphical user interface, and wherein movement of the single slider by a user results in the at least one controller simultaneously updating the operating parameters display of laser energy, laser power, a pulse frequency, air delivery, and water delivery.

* * * * *